US012629354B2

(12) United States Patent (10) Patent No.: US 12,629,354 B2
Hong et al. (45) Date of Patent: May 19, 2026

(54) SUSTAINED-RELEASE PHARMACEUTICAL COMPOSITIONS COMPRISING OF A SEDATIVE DRUG AND USES THEREOF

(71) Applicants: TAIWAN LIPOSOME CO., LTD., Taipei City (TW); TLC BIOPHARMACEUTICALS, INC., South San Francisco, CA (US)

(72) Inventors: Keelung Hong, South San Francisco, CA (US); Walter Gwathney, South San Francisco, CA (US); Hao-wen Kao, South San Francisco, CA (US); Yi-yu Lin, South San Francisco, CA (US)

(73) Assignees: TAIWAN LIPOSOME CO., LTD., Taipei City (TW); TLC BIOPHARMACEUTICALS, INC., South San Francisco, CA (US)

( * ) Notice: Subject to any disclaimer, the term of this patent is extended or adjusted under 35 U.S.C. 154(b) by 1164 days.

(21) Appl. No.: 17/274,850

(22) PCT Filed: Sep. 12, 2019

(86) PCT No.: PCT/US2019/050767
§ 371 (c)(1),
(2) Date: Mar. 10, 2021

(87) PCT Pub. No.: WO2020/056102
PCT Pub. Date: Mar. 19, 2020

(65) Prior Publication Data
US 2022/0054455 A1 Feb. 24, 2022

Related U.S. Application Data

(60) Provisional application No. 62/730,713, filed on Sep. 13, 2018.

(51) Int. Cl.
*A61K 31/4164* (2006.01)
*A61K 9/127* (2025.01)
*A61K 47/18* (2017.01)
*A61K 47/26* (2006.01)
*A61K 47/28* (2006.01)

(52) U.S. Cl.
CPC .......... *A61K 31/4164* (2013.01); *A61K 9/127* (2013.01); *A61K 47/186* (2013.01); *A61K 47/26* (2013.01); *A61K 47/28* (2013.01)

(58) Field of Classification Search
CPC ........ A61K 9/127; A61K 47/26; A61K 47/28; A61K 31/4164; A61K 47/186
See application file for complete search history.

(56) References Cited

U.S. PATENT DOCUMENTS

| | | | |
|---|---|---|---|
| 6,514,516 B1 | 2/2003 | Chasin et al. | |
| 9,895,313 B2* | 2/2018 | Zhu | A61K 31/704 |
| 2004/0156889 A1 | 8/2004 | Hu et al. | |
| 2008/0003276 A1* | 1/2008 | Barenholz | A61P 11/02 |
| | | | 514/180 |
| 2013/0202686 A1 | 8/2013 | Yamashita et al. | |
| 2014/0005243 A1 | 1/2014 | Garcia da Rocha et al. | |
| 2014/0220110 A1 | 8/2014 | Hayes et al. | |
| 2014/0271822 A1 | 9/2014 | McGhee et al. | |
| 2015/0086484 A1 | 3/2015 | Hanes et al. | |
| 2016/0030340 A1 | 2/2016 | Kan et al. | |
| 2019/0070115 A1* | 3/2019 | Rwei | A61K 31/4174 |

FOREIGN PATENT DOCUMENTS

| | | |
|---|---|---|
| CN | 101756902 A | 6/2010 |
| CN | 105163720 A | 12/2015 |
| EP | 1105098 B1 | 3/2007 |
| JP | 2016513655 A | 5/2016 |
| JP | 2016518340 A | 6/2016 |
| WO | 2012091054 A1 | 6/2014 |
| WO | 2016191547 A1 | 12/2016 |
| WO | 2017062875 A1 | 4/2017 |
| WO | 2017123588 A1 | 7/2017 |
| WO | 2020028475 A1 | 2/2020 |
| WO | 2020033195 A1 | 2/2020 |

OTHER PUBLICATIONS

Seyrek, et al. "Interaction between dexmedetomidine and alpha-adrenergic receptors" Journal of Cardiothoracic and Vascular Anesthesia 2011; 25 (5): pp. 856-862. DOI: 10.1053/.jvca.2011.06.006 (Year: 2011).*

Czock et al. "Pharmacokinetics and pharmacodynamics of systemically administered glucocorticoids" Clinical Pharmacokinetics 2005; 44 (1): pp. 61-98. DOI: 10.2165/00003088-200544010-00003 (Year: 2005).*

Office action for related China Application No. 201980057845.5, mailed May 25, 2023.

Sheng Tu et al. "A Mathematical Relationship for Hydromorphone Loading into Liposomes with Trans-Membrane Ammonium Sulfate Gradients," J Pharm Sci., Jun. 2010, pp. 2,672-2,680, vol. 99, No. 6.

"Hydromorphone," Wikipedia.com, accessed by US/ISA Aug. 16, 2018, downloaded Mar. 5, 2021.

"Sedative," Wikipedia.com, accessed by US/ISA Jun. 6, 2018, downloaded Mar. 5, 2021.

"Cholesterol," Wikipedia.com, accessed by US/ISA, Aug. 26, 2018, downloaded Mar. 5, 2021.

International Search Report & Written Opinion for PCT/US2019/050767, mailed Jan. 27, 2020.

(Continued)

*Primary Examiner* — Sahana S Kaup
*Assistant Examiner* — Toriana N. Vigil
(74) *Attorney, Agent, or Firm* — Pilloff Passino & Cosenza LLP; Rachel Pilloff; Sean Passino

(57) ABSTRACT

The present invention relates to a pharmaceutical composition comprising at least one liposome, a trapping agent and a sedative drug with a high drug to lipid ratio and a high encapsulation efficiency. Also provided are the methods to sedate or treat pain in a subject in need thereof by administering the pharmaceutical composition disclosed herein.

19 Claims, 4 Drawing Sheets

(56) References Cited

OTHER PUBLICATIONS

Office Action for related Taiwan application, mailed May 19, 2020.

Alina Y. Rwei et al., "Prolonged Duration Local Anesthesia Using Liposomal Bupivacaine Combined With Liposomal Dexamethasone and Dexmedetomidine," Preclinical Pharmacology, Apr. 2018, pp. 1,170-1,175, vol. 126, No. 4.

Lisa Krugner-Higby et al., "Pharmacokinetics and Behavioral Effects of an Extended-Release, Liposome-Encapsulated Preparation of Oxymorphone in Rhesus Macaques," Journal of Pharmacology and Experimental Therapeutics, Apr. 6, 2009, pp. 135-141, vol. 330, No. 1.

Chen Jun et al., "Preparation and pharmacokinetic investigation of propranolol-loaded elastic liposomes composed of DP-PC and SPC," Chinese Pharmaceutical Journal, Oct. 22, 2013, pp. 1,761-1,765, vol. 48, No. 20.

G.J. Grant MD et al., "A novel liposomal bupivacaine formulation using an ammonium sulfate gradient," Regional Anesthesia and Pain Medicine, May 1, 1999, p. 42, vol. 24, No. 3.

Chapter 6. Drug Therapy in Neuropsychiatry, Section I, Assesment and Treatments: In: Randolph B. Shiffer; Stephen M. Rao; Barry S. Fogel: "Neuropsychiatry," Jan. 2003.

Office action for related Europe Application No. 19860619.6, mailed May 11, 2022.

Office action for related India Application No. 202117010233, mailed Dec. 7, 2022.

Office action for China Application No. 201980057845.5, mailed Nov. 24, 2023.

Hearing Notice for India Application No. 202117010233, mailed Sep. 19, 2023.

Office Action for Japan Application No. 2021-513789, mailed Oct. 3, 2023.

Surojit Sur, et al., Remote loading of preencapsulated drugs into stealth liposomes. Proc Natl Acad Sci U S A. Feb. 11, 2014;111(6):2283-88. doi: 10.1073/pnas.1324135111. Epub Jan. 28, 2014. PMID: 24474802; PMCID: PMC3926059.

Rebekah K Franklin, et al., A Novel Loading Method for Doxycycline Liposomes for Intracellular Drug Delivery: Characterization of In Vitro and In Vivo Release Kinetics and Efficacy in a J774A.1 Cell Line Model of Mycobacterium smegmatis Infection, Drug Metab Dispos. Aug. 2015; 43(8):1236-45. doi: 10.1124/dmd.115.063602. Epub Jun. 1, 2015. Erratum in: Drug Metab Dispos. Nov. 2015;43(11):1805. doi: 10.1124/dmd.115.063602err. Erratum in: Drug Metab Dispos. Apr. 2016;44(4):606. doi: 10.1124/dmd.115.063602err2. PMID: 26033620; PMCID: PMC4518064.

Tin Hou, et al., Research Advances in the Preparation of Various Lipid Vesicles Using Ammonium Sulfate Gradient Method, China Pharmacist, 2009, vol. 12, No. 12, pp. 1723-1725.

* cited by examiner

A, Free Ropivacaine
B, Free Ropivacaine + L-DEX
C, Liposomal Ropivacaine Composition
D, Liposomal Ropivacaine Composition + L-DEX Group A Head

C ○   ◉ D

D ◉   ○ C

A ▦

Tail

Group B

Head

C ○   ◉ D

D ◉   ○ C

B ▥

Tail

A, Saline
B, L-DEX
C, Free Ropivacaine
D, Liposomal Ropivacaine Composition

▲ Saline + Ropivacaine
△ L-DEX + Free Ropivacaine
● Saline + Liposomal Ropivacaine Composition
○ L-DEX + Liposomal Ropivacaine Composition

SUSTAINED-RELEASE PHARMACEUTICAL COMPOSITIONS COMPRISING OF A SEDATIVE DRUG AND USES THEREOF

CROSS-REFERENCE TO RELATED APPLICATION

This application claims the benefit of U.S. Application No. 62/730,713, filed on 13 Sep. 2018, the entire disclosure of which is incorporated herein by reference.

TECHNICAL FIELD

The present invention is directed to a sustained-release pharmaceutical composition comprising of a sedative drug with a high drug to lipid ratio and a high encapsulation efficiency using at least one trapping agent. The high drug to lipid ratio, high encapsulation efficiency and sustained release profile of the claimed pharmaceutical composition reduce the frequency of drug administration, increase patient compliance and improve the therapeutic outcome.

BACKGROUND

Dexmedetomidine is a highly selective $\alpha_2$-adrenergic receptor agonist with analgesic and sedative properties without significant respiratory depression. It has been approved for treating anxiety and procedural sedation in humans and companion animals in many countries. This medication is typically administered as an intravenous or intramuscular injection, although a transdermal patch has been proposed (WO2015054058A1).

Liposomes have been widely used for developing sustained-release formulations for various drugs. Drug loading into liposomes can be attained either passively (the drug is encapsulated during liposome formation) or remotely/actively (creating a transmembrane pH- or ion-gradient during liposome formation and then the drug is loaded by the driving force generated from the gradients after liposome formation) (U.S. Pat. Nos. 5,192,549 and 5,939,096). Although the general methods of drug loading into liposomes are well documented in the literature, only a handful of therapeutic agents were successfully loaded into liposomes with high drug to lipid ratio and high encapsulation efficiency, which are important to sustain the release of the encapsulated therapeutic agent. Numerous factors can affect the drug to lipid ratio and encapsulation efficiency of liposomes, including but not limited to, the physical and chemical properties of the therapeutic agent, for example, hydrophilic/hydrophobic characteristics, dissociation constant, solubility and partition coefficient, lipid composition, trapping agent, reaction solvent, and particle size (Proc. Natl. Acad. Sci USA. 2014; 111(6): 2283-2288 and Drug Metab. Dispos. 2015:43 (8):1236-45).

There remains an unmet need for a sustained release formulation with a high drug to lipid ratio and drug encapsulation efficiency to prolong the effect of the sedative drug, reduce the dosage and side effects of co-administered analgesic and/or anesthetic agents and improve the therapeutic outcome. The present invention addresses this need and other needs.

SUMMARY OF THE INVENTION

In one embodiment, a sustained release pharmaceutical composition comprises (a) at least one first liposome comprising a bilayer membrane: (b) a trapping agent; and (c) a sedative drug, wherein the bilayer membrane comprises at least one lipid and the molar ratio of the drug to the lipid is equal to or higher than about 0.02 is provided.

In another embodiment, methods are provided for sedating a subject, comprising the steps of administering the pharmaceutical composition described herein to a subject in need thereof.

According to another embodiment, methods are provided for treating pain in a subject, comprising the steps of administering (a) the pharmaceutical composition described herein and (b) an anesthetic, an analgesic or a combination thereof to a subject in need thereof.

Also provided are the uses of the pharmaceutical composition described herein in the manufacture of a medicament for sedation or reducing pain.

Further provided is a medicament for sedating a subject or treating pain in a subject, comprising a therapeutically effective amount of the pharmaceutical composition described herein.

The terms "invention," "the invention," "this invention" and "the present invention" used in this patent are intended to refer broadly to all the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification, any or all drawings and each claim.

A further understanding of the nature and advantages of the present invention may be realized by reference to the remaining portions of the specification and the drawings.

DETAILED DESCRIPTION OF THE INVENTION

Figure 1A:
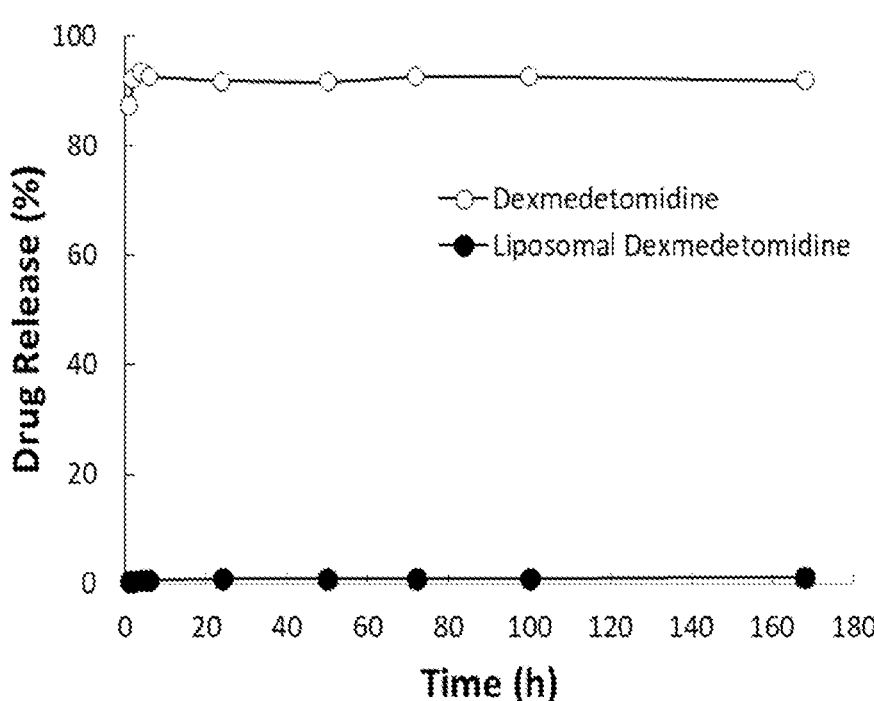
FIG. 1A and FIG. 1B are line graphs showing the release profiles of liposomal dexmedetomidine and free dexmedetomidine (dexmedetomidine) in plasma free environment (FIG. 1A) and in human plasma (FIG. 1B).

As employed above and throughout the disclosure, the following terms, unless otherwise herein, the singular forms "a", "an" and "the" include the plural reference unless the context clearly indicates otherwise.

All numbers herein may be understood as modified by "about." As used herein, the term "about" refers to a range of ±10% of a specified value.

An "effective amount," as used herein, refers to a dose of the pharmaceutical composition to sedate a subject or to treat pain in combination with an anesthetic and/or an analgesic to decrease the dosing frequency or dose of the anesthetic or analgesic. The term "effective amount" and "therapeutically effective amount" are used interchangeably.

The term "treating," "treated," or "treatment," as used herein, includes preventative (e.g. prophylactic), palliative, and curative methods, uses or results. The terms "treatment" or "treatments" can also refer to compositions or medicaments. In an embodiment, the term "treating" encompasses provide sedation or reduce or complete amelioration of the symptoms or signs of anxiety. In another embodiment, the term "treating" encompasses reducing or delaying one or more symptoms or signs of pain or the complete amelioration of pain as detected by art-known techniques, such as pain score. Thus, the reduction of pain can be about 1, 5, 10, 20, 30, 40, 50, 60, 70, 80, 90, 100%, or any amount of reduction in between.

The term "adjuvant," as used herein, involves the use of the pharmaceutical compositions or medicaments described herein as adjuvants to enhance the effect of an anesthetic or analgesic and/or reduce the anesthetic or analgesic requirements. Examples of anesthetic, including but not limited to, general anesthetics such as induction agents (e.g., ketamine, propofol and thiopentone), muscle relaxants (e.g., atracurium, pancuronium, rocuronium, suxamethonium and vecuronium), inhalational anaesthetics (e.g., desflurane, enflurane, isoflurane and sevoflurane), regional such as ropivacaine, levobupivacaine and bupivacaine, local anesthetics such as ropivacaine, lidocaine and bupivacaine. Non-limiting examples of analgesic include opioid analgesic such as morphine, fentanyl, and codeine or non-opioid analgesic such as non-steroidal anti-inflammatory drug (NSAID) and paracetamol.

The term "subject" can refer to a vertebrate requiring sedation or treatment of anxiety or pain or to a vertebrate deemed to be in need of sedation or treatment of anxiety or pain. Subjects include all warm-blooded animals, such as mammals, such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, mouse, rabbit, rat, gerbil, guinea pig, etc.). Thus, veterinary uses and medical formulations are contemplated herein.

Liposome

The terms "liposome," "liposomal" and related terms as used herein are characterized by an interior aqueous space sequestered from an outer medium by one or more bilayer membranes forming a vesicle. In certain embodiments, the interior aqueous space of the liposome is substantially free of a neutral lipid, such as triglyceride, non-aqueous phase (oil phase), water-oil emulsions, a second liposome or other mixtures containing non-aqueous phase. Non-limiting examples of liposomes include small unilamellar vesicles (SUV), large unilamellar vesicles (LUV), and multi-lamellar vesicles (MLV) with an average diameter ranges from 50-20 μm, 50-450 nm, 50-400 nm, 50-350 nm, 50-300 nm, 50-250 nm, 50-200 nm, 100-500 nm, 100-450 nm, 100-400 nm, 100-350 nm, 100-300 nm, 100-250 nm or 100-200 nm.

Bilayer membranes of liposomes are typically formed by at least one lipid, i.e. amphiphilic molecules of synthetic or natural origin that comprise spatially separated hydrophobic and hydrophilic domains. Examples of lipid, including but not limited to, dialiphatic chain lipids, such as phospholipids, diglycerides, dialiphatic glycolipids, single lipids such as sphingomyelin and glycosphingolipid, and combinations thereof. Examples of phospholipid according to the present disclosure include, but not limited to, 1,2-dilauroyl-sn-glycero-3-phosphocholine (DLPC), 1,2-dimyristoyl-sn-glycero-3-phosphocholine (DMPC), 1,2-dipalmitoyl-sn-glycero-3-phosphocholine (DPPC), 1-palmitoyl-2-stearoyl-sn-glycero-3-phosphocholine (PSPC), 1-palmitoyl-2-oleoyl-sn-glycero-3-phosphatidylcholine (POPC), 1,2-distearoyl-sn-glycero-3-phosphocholine (DSPC), 1,2-dioleoyl-sn-glycero-3-phosphocholine (DOPC), hydrogenated soy phosphatidylcholine (HSPC), 1,2-dimyristoyl-sn-glycero-3-phospho-(1'-rac-glycerol) (sodium salt) (DMPG), 1,2-dipalmitoyl-sn-glycero-3-phospho-(1'-rac-glycerol) (sodium salt) (DPPG), 1-palmitoyl-2-stearoyl-sn-glycero-3-phospho-(1'-rac-glycerol) (sodium salt) (PSPG), 1,2-distearoyl-sn-glycero-3-phospho-(1'-rac-glycerol) (sodium salt) (DSPG), 1,2-dioleoyl-sn-glycero-3-phospho-(1'-rac-glycerol) (DOPG), 1,2-dimyristoyl-sn-glycero-3-phospho-L-serine (sodium salt) (DMPS), 1,2-dipalmitoyl-sn-glycero-3-phospho-L-serine (sodium salt) (DPPS), 1,2-distearoyl-sn-glycero-3-phospho-L-serine (sodium salt) (DSPS), 1,2-dioleoyl-sn-glycero-3-phospho-L-serine (DOPS), 1,2-dimyristoyl-sn-glycero-3-phosphate (sodium salt) (DMPA), 1,2-dipalmitoyl-sn-glycero-3-phosphate (sodium salt) (DPPA), 1,2-distearoyl-sn-glycero-3-phosphate (sodium salt) (DSPA), 1,2-dioleoyl-sn-glycero-3-phosphate (sodium salt) (DOPA), 1,2-dipalmitoyl-sn-glycero-3-phosphoethanolamine (DPPE), N-(carbonyl-methoxypolyethyleneglycol)-1,2-dipalmitoyl-sn-glycero-3-phosphoethanolamine (PEG-DPPE), 1-palmitoyl-2-oleoyl-sn-glycero-3-phosphoethanolamine (POPE), 1,2-distearoyl-sn-glycero-3-phosphoethanolamine (DSPE), N-(carbonyl-methoxypolyethyleneglycol)-1,2-distearoyl-sn-glycero-3-phosphoethanolamine (PEG-DSPE), 1,2-dioleoyl-sn-glycero-3-phosphoethanolamine (DOPE), 1,2-dipalmitoyl-sn-glycero-3-phospho-(1'-myo-inositol) (ammonium salt) (DPPI), 1,2-distearoyl-sn-glycero-3-phosphoinositol (ammonium salt) (DSPI), 1,2-dioleoyl-sn-glycero-3-phospho-(1'-myo-inositol) (ammonium salt) (DOPI), cardiolipin, L-α-phosphatidylcholine (EPC), and L-α-phosphatidylethanolamine (EPE). In some embodiments, the lipid is a lipid mixture of one or more of the foregoing lipids, or mixtures of one or more of the foregoing lipids with one or more other lipids not listed above, membrane stabilizers or antioxidants.

In certain embodiments, the mole percent of the lipid in the bilayer membrane of the first liposome is about 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45 or any value or range of values therebetween (e.g., about 45-85%, about 45-80%, about 45-75%, about 45-70%, about 45-65%, about 50-85%, about 50-80%, about 50-75%, about 50-70% or about 50-65%).

In some embodiments, the lipid of the bilayer membrane of the first liposome comprises a mixture of a first lipid and a second lipid. In some embodiments, the first lipid is selected from the group consisting essentially of phosphatidylcholine (PC), HSPC, DSPC, DPPC, DMPC, PSPC and combination thereof and the second lipid is selected from the group consisting essentially of a phosphatidylethanolamine, phosphatidylglycerol, PEG-DSPE, DPPG and combination thereof. In other embodiments, the mole percent of the first lipid in the bilayer membrane is about 84.9, 84.5, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40 or any value or range of values therebetween (e.g., about 40-84.9%, about 40-84.5%, about 40-80%, about 40-75%, about 40-70%, about 40-65% or about 40-60%) and the mole percent of the second lipid in the bilayer membrane is about 25, 24, 23, 22, 21, 20, 19, 18, 17, 16, 15, 14, 13, 12, 11, 10, 9, 8, 7, 6, 5, 4, 3, 2, 1, 0.9, 0.5, 0.1 or any value or range of values therebetween (e.g., about 0.1-25% or about 0.5-25%).

The bilayer membrane of the liposome further comprises less than about 55 mole percentage of steroids, preferably cholesterol. In certain embodiments, the mole % of steroid, such as cholesterol, in the bilayer membrane is about 15-55%, about 20-55%, about 25-55%, about 15-50%, about 20-50%, about 25-50%, about 15-45%, about 20-45%, about 25-45%, about 15-40%, about 20-40% or about 25-40%.

In one exemplary embodiment, the mole % of the lipid and cholesterol in the bilayer membrane of the first liposome is about 45-85%: 15-55% or about 50-80%: 20-50%. In another exemplary embodiment, the mole % of the first lipid, the second lipid and cholesterol in the bilayer membrane of the first liposome is about 40-84.9%: 0.1%-25%: 15-55%, 40-75%: 0.1-25%: 20-50% or 40-70%: 0.1-25%: 25-50% and the first lipid is HSPC, DMPC, DSPC or combination thereof and the second lipid is DSPE-PEG2000, DPPG or combination thereof.

Remote Loading

The term "remote loading" as used herein is a drug loading method which involves a procedure to transfer drugs from the external medium across the bilayer membrane of the liposome to the interior aqueous space by a polyatomic ion-gradient. Such gradient is generated by encapsulating at least one polyatomic ion as a trapping agent in the interior aqueous space of the liposome and replacing the outer medium of the liposome with an external medium with a lower polyatomic ion concentration, for example, pure water, sucrose solution and saline, by known techniques, such as column separation, dialysis or centrifugation. A polyatomic ion gradient is created between the interior aqueous space and the external medium of the liposomes to trap the therapeutic agent in the interior aqueous space of the liposomes. Exemplary polyatomic ion as trapping agents include, but are not limited to, sulfate, sulfite, phosphate, hydrogen phosphate, molybdate, carbonate and nitrate. Exemplary trapping agents include, but are not limited to, ammonium sulfate, ammonium phosphate, ammonium molybdate, ammonium sucrose octasulfate, triethylammonium sucrose octasulfate and dextran sulfate.

In an embodiment, the concentration of ammonium sulfate is about 100 to about 600 mM, about 150 to about 500 mM or about 200 to about 400 mM. In another embodiment, the concentration of triethylammonium sucrose octasulfate is about 10 to about 200 mM or about 50 to about 150 mM. In yet another embodiment, the concentration of ammonium phosphate is about 100 to about 600 mM, about 150 to about 500 mM or about 200 to about 400 mM. In yet another embodiment, the concentration of dextran sulfate is about 0.1 to 20 mM or about 1 to 10 mM.

In accordance with the invention, the liposomes can be prepared by any of the techniques now known or subsequently developed. For example, the MLV liposomes can be directly formed by a hydrated lipid film, spray-dried powder or lyophilized cake of selected lipid compositions with trapping agent: the SUV liposomes and LUV liposomes can be sized from MLV liposomes by sonication, homogenization, microfluidization or extrusion.

Pharmaceutical Compositions

The present invention is directed to a sustained release pharmaceutical composition, comprising (a) at least one first liposome comprising a bilayer membrane: (b) a trapping agent; and (c) a sedative drug, wherein the bilayer membrane comprises at least one lipid and the molar ratio of the drug to the lipid is above or equal to 0.02.

In one embodiment, the sustained release pharmaceutical composition further comprises at least one pharmaceutically acceptable excipient, diluent, vehicle, carrier, medium for the active ingredient, a preservative, cryoprotectant or a combination thereof. In one exemplary embodiment, the weight percent of the bilayer membrane in the pharmaceutical composition is about 0.1-12%: the weight percent of the trapping agent in the pharmaceutical composition is about 0.1-10%; and the weight percent of the pharmaceutically acceptable excipient (such as sucrose, histidine, sodium chloride and ultrapure water), diluent, vehicle, carrier, medium for the active ingredient, a preservative, cryoprotectant or a combination thereof in the pharmaceutical composition is about 80.0-99.9%.

In one embodiment, the sedative drug is an alpha-2-adrenoceptor ($\alpha_2$) agonist. Non-limiting examples of $\alpha_2$ agonist include clonidine, fadolmidine, guanabenz, guanoxabenz, guanethidine, guanfacine, medetomidine, methyldopa, methylnorepinephrine, tizanidine, xylazine and dexmedetomidine. The sustained release profile of the pharmaceutical composition prolongs the half-life and the therapeutic efficacy by maintaining the therapeutic concentration of the sedative drug, and hence, reduces the dosage and/or the frequency of sedative drug administration. The sustained release profile of the pharmaceutical composition enhances the effect of the co-administered anesthesia or analgesic agent and reduces the dosage and/or the frequency of administration of co-administered anesthesia or analgesic agent.

In one aspect, the sustained release profile of the pharmaceutical composition is owed to a drug encapsulation efficiency of at least 40%, 50%, 55%, 60%, 65%, 70% or 75%.

In another aspect, sustained release profile of the pharmaceutical composition is due to the higher drug to lipid molar ratio. In an exemplary embodiment, the molar ratio of the sedative drug to the one or more lipids is above or equal to 0.02, 0.03, 0.04, 0.05, 0.06, 0.07, 0.08 or 0.09, alternatively from 0.02 to 10, from 0.02 to 5, from 0.02 to 2, from 0.02 to 1, from 0.05 to 10, from 0.05 to 5, from 0.05 to 2, from 0.05 to 1, from 0.05 to 0.5, from 0.09 to 10, from 0.09 to 5, from 0.09 to 2, from 0.09 to 1 or from 0.09 to 0.5.

In yet another aspect, the half-life of the sedative drug is extended by at least 2-fold compared to that of the free sedative drug.

In some embodiments, the pharmaceutical composition further comprises an analgesic, an anesthetic or the combination thereof. In an exemplary embodiment, the analgesic, the anesthetic or the combination thereof is not encapsulated in a liposome. In another exemplary embodiment, the analgesic, the anesthetic or the combination thereof is encapsulated in a second liposome. In an exemplary embodiment, the second liposome is a multilamellar vesicle disclosed in PCT/US18/48329, the content of which is incorporated herein in its entirety. The second liposome comprises at least one lipid and cholesterol at a molar ratio of from 1:0.01 to 1:1. The term "encapsulated" and "entrapped" are used interchangeably.

The invention also provides methods to sedate a subject, comprise the step of administration of an effective amount of the pharmaceutical composition as described herein to the subject in need thereof.

The invention further provides methods to reduce or treat pain, by administering (a) an effective amount of the pharmaceutical composition as described herein and (b) an analgesic, an anesthetic or the combination thereof to a subject in need thereof, whereby the pain is reduced. The pharmaceutical composition enhances and sustains the effect of the analgesic, the anesthetic or the combination thereof, so the dose and the administering frequency of the analgesic or anesthetic can be reduced while the subject has a longer pain-free period compared to using the anesthetic or analgesic in monotherapy regimen. The pharmaceutical composition can be administered before, after or simultaneously with the anesthetic or analgesic.

The pharmaceutical composition is formulated to be suitable for cutaneous injection, such as subcutaneous, subdermal, transdermal, intradermal or intramuscular route. The pharmaceutical composition is also formulated to be administered as a transdermal patch or administered by intravenous, oral or inhalation route.

The dosage of the pharmaceutical composition of the present invention can be determined by the skilled person in the art according to the embodiments. Unit doses or multiple dose forms are contemplated, each offering advantages in certain clinical settings. According to the present invention, the actual amount of the pharmaceutical composition to be administered can vary in accordance with the age, weight, condition of the subject to be treated, any exiting medical conditions, and on the discretion of medical professionals.

In one embodiment, the pharmaceutical compositions disclosed herein significantly extended the release of the encapsulated therapeutic agent. For example, the pharmaceutical composition of the present invention extended the half-life of intramuscularly (IM) administered dexmedetomidine to 4.07 hours in rats (as disclosed in Example 4) compared to the FDA approved dexmedetomidine formulation for IM injection (1.5 hours in rats, Precedex® New Drug Application submitted package, Abbot Laboratories Corporation, Application No.: 21-038). These pharmaceutical compositions are developed to reduce the administration frequency of the sedative drug as well as reduce the administration frequency and/or dosage of the co-administered anesthetic or analgesic.

EXAMPLES

Embodiments of the present invention are illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the invention. During the studies described in the following examples, conventional procedures were followed, unless otherwise stated.

Example 1. Preparation of Liposomal Dexmedetomidine Formulation

Empty liposomes were prepared by a lipid film hydration-extrusion method. HSPC, cholesterol, and DSPE-PEG2000 (mole percent 59.5/39.6/0.9) were dissolved in chloroform and a thin lipid film was formed by removing the organic solvent under vacuum in a rotary evaporator. The dry lipid film was rehydrated in 300 mM ammonium sulfate at 60° C. for 30 min and liposomes were formed with ammonium sulfate encapsulated in the aqueous core. After six freeze-thaw cycles between liquid nitrogen and water at 60° C., the liposomes were subsequently extruded ten times through polycarbonate filter membranes with a pore size of 0.2 μm. Unencapsulated ammonium sulfate was removed by dialysis against a 9.4% sucrose solution.

A reaction mixture containing 4.0 mg/mL of dexmedetomidine hydrochloride (Ark Pharm), empty liposomes of the preceding paragraph containing 40.0 mM of lipids and 10 mM histidine buffer (pH 6.5) was incubated at 60° C. for 30 min. The unencapsulated dexmedetomidine hydrochloride was separated by a Sephadex™ G-50 Fine gel (GE Healthcare) or dialysis bag (Spectrum Labs) against a 9.4% sucrose solution to obtain the liposomal dexmedetomidine formulation. The concentrations of the encapsulated dexmedetomidine hydrochloride and the lipid of the liposomal dexmedetomidine formulation were measured using a HPLC and an ultraviolet/visible (UV/Vis) spectrophotometer and used to calculate the drug to lipid molar ratio (D/L) of the liposomal dexmedetomidine formulation.

The encapsulation efficiency was calculated by the drug to lipid molar ratio (D/L) of liposomal dexmedetomidine formulation compared to that of the nominal D/L of reaction mixture, which was calculated by dividing the concentration of dexmedetomidine by the lipid concentration of empty liposome. The particle size distribution was measured by a dynamic light scattering instrument (Zetasizer Nano-ZS90, Malvern).

Using 300 mM ammonium sulfate as a trapping agent, the liposomal dexmedetomidine formulation achieved a final D/L of 0.32 and an encapsulation efficiency of 76.6%. The mean diameter of the liposomes was 202.5 nm.

Example 2. The Effect of Different Trapping Agents on Dexmedetomidine Loading Profile The liposome formulations were prepared according to Example 1, with the following trapping agents: (1) 75 mM of triethylammonium sucrose octasulfate, (2) 300 mM of ammonium sulfate, (3) 200 mM ammonium phosphate and (4) 7.0 mM of dextran sulfate.

Table 1 shows the effect of different trapping agents on drug loading.

TABLE 1

| The drug loading profile of different trapping agents | | | | |
|---|---|---|---|---|
| Bilayer Membrane (mole percent) | Trapping Agent | Purified D/L (mole/ mole) | EE (%) | Average Particle Size (nm) |
| HSPC/cholesterol (60/40) | 1 | 0.37 | 87.1 | 206.3 |
| HSPC/cholesterol/DSPE-PEG2000 (41.8/37.2/21.0) | 1 | 0.29 | 69.0 | 229.9 |
| HSPC/cholesterol/DSPE-PEG2000 (59.5/39.6/0.9) | 2 | 0.32 | 76.6 | 202.5 |
| DMPC/cholesterol/DSPE-PEG2000 (59.5/40/0.5) | 2 | 0.09 | 44.6 | 181.5 |
| HSPC/cholesterol/DPPG (59.5/39.6/0.9) | 2 | 0.22 | 52.0 | 223.2 |
| DPPC/cholesterol/DSPE-PEG2000 (57/34.3/8.7) | 3 | 0.18 | 41.7 | 184.0 |
| DSPC/cholesterol/DSPE-PEG2000 (59.5/39.6/0.9) | 4 | 0.19 | 46.0 | 231.5 |

EE = encapsulation efficiency.

Example 3. Prolonged Release Profile of Liposomal Dexmedetomidine Formulation Two in vitro release systems were used in the study, the first system was the plasma free environment and the second system was the human plasma environment. To setup the first in vitro release system, 0.5 mL of liposomal dexmedetomidine formulation, prepared according to Example 2 (first row in Table 1), and 0.5 mL of free dexmedetomidine hydrochloride were placed in separate dialysis bags (Spectra/Pro®6 dialysis membrane, MWCO 50 kDa, Spectrum Labs) and both ends of the dialysis bags were sealed. To setup the second in vitro release system, 0.2 mL of liposomal dexmedetomidine formulation prepared according to Example 1 and 0.2 mL of free dexmedetomidine hydrochloride were placed in separate dialysis bags, each containing 0.8 mL of human plasma (Valley Biomedical, Inc.) and both ends of dialysis bags were sealed. Each dialysis bag was immersed in 20 mL of PBS at pH 7.4 in a 50-mL centrifuge tube and incubated at 37±1° C. water bath for 168 or 72 hours. At designated time points after incubation (1, 2, 4, 6, 24, 50, 72, 100 and 168 hours of first system and 1, 2, 4, 8, 24, 48 and 72 hours of second system), 1.0 mL aliquot from the 20-mL PBS was sampled and 1.0 mL of fresh PBS was added to replenish the sampling aliquot. Drug concentrations of the sampled aliquots at each time point were analyzed using HPLC to create the in vitro release profile of the tested formulations.

In the first in vitro release system, almost one hundred percent (100%) of dexmedetomidine was released from the free dexmedetomidine formulation through the plasma free dialysis bag within 2 hours. In contrast, less than 2% of dexmedetomidine was released from the liposomal dexmedetomidine formulation through the plasma free dialysis bag over 168 hours, see FIG. 1A.

Figure 1B:
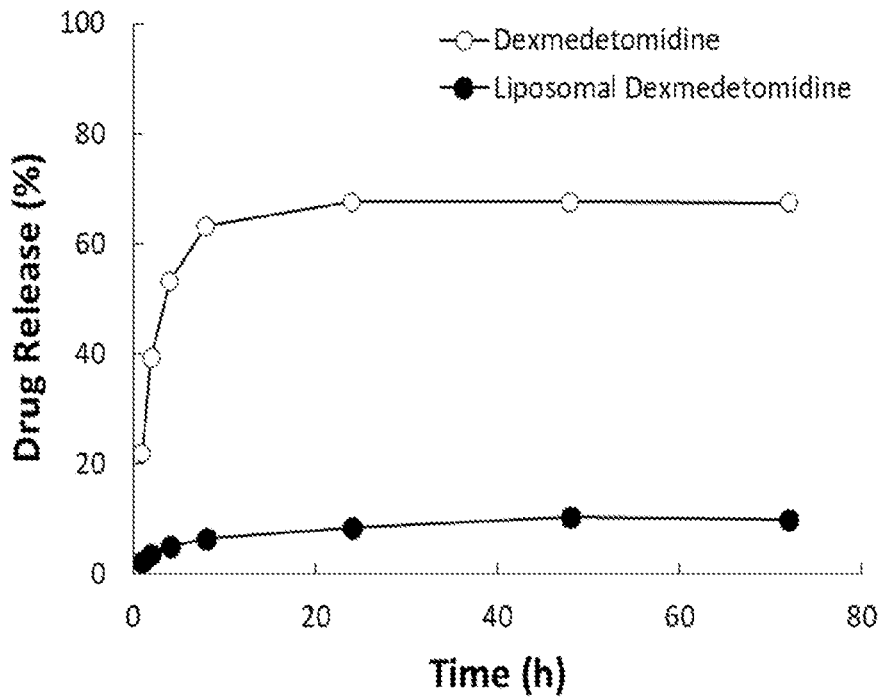

Referring to FIG. 1B, in the second in vitro release system (human plasma), about 70% of dexmedetomidine was released from free dexmedetomidine formulation within 8 hours, whereas only 10% of dexmedetomidine was releases from the liposomal dexmedetomidine formulation over a 72-hour period.

Example 4. Pharmacokinetics (PK) Study of Liposomal Dexmedetomidine Formulation An in vivo PK evaluation of the liposomal dexmedetomidine formulation was performed using Jugular vein cannulated (JVC) female Sprague-Dawley rats (7-8 weeks old).

The rats were housed in a holding room which operated on a 12-hr light/12-hr dark circadian cycle with free access to water and food.

The rats were divided into two groups (n=4 in each group), one group received intramuscular (IM) injection of 100 µg/kg of free dexmedetomidine hydrochloride, prepared by dissolving the dexmedetomidine hydrochloride in 9.4% sucrose solution with a final concentration of 250 µg/mL. The other group received IM injection of 106 µg/kg of liposomal dexmedetomidine hydrochloride, prepared according to Example 1. Blood samples were collected at 15, 30 min, 1, 2, 4, 8, 24, 48, and 72 hours post-injection. Plasma samples were obtained by centrifugation, kept frozen at −80° C. and analyzed using liquid chromatography-tandem mass spectrometry. The plasma concentrations versus time curves were analyzed using a noncompartmental analysis model in PKSolver (Comput. Methods Programs Biomed. 2010; 99(3):306-314). The PK parameters of the two dexmedetomidine formulations are summarized in Table 2.

The results in Table 2 show the $C_{max}$ of liposomal dexmedetomidine formulation was 47.5% of that of free dexmedetomidine, and the half-life ($t_{1/2}$) of liposomal dexmedetomidine formulation was significantly longer compared to that of the free dexmedetomidine. The area under the curve ($AUC_{0-t}$) indicates 63.1% of dexmedetomidine was released from liposomal dexmedetomidine formulation 8 hours post-injection whereas the $AUC_{0-t}$ of free dexmedetomidine indicates 100% of dexmedetomidine was released 8 hours post-injection.

TABLE 2

| PK parameters derived from rats after single intramuscular injection of free dexmedetomidine and liposomal dexmedetomidine | | | |
|---|---|---|---|
| Parameters | Unit | Free Dexmedetomidine | Liposomal Dexmedetomidine Formulation |
| $t_{1/2}$ | h | 2.36 | 4.07 |
| $C_{max}$ | ng/ml | 11.0 | 5.22 |
| $AUC_{0-t}$ | h × ng/mL | 31.4 | 19.8 |
| $AUC_{0-inf}$ | h × ng/mL | 35.1 | 27.7 |

Figure 2:
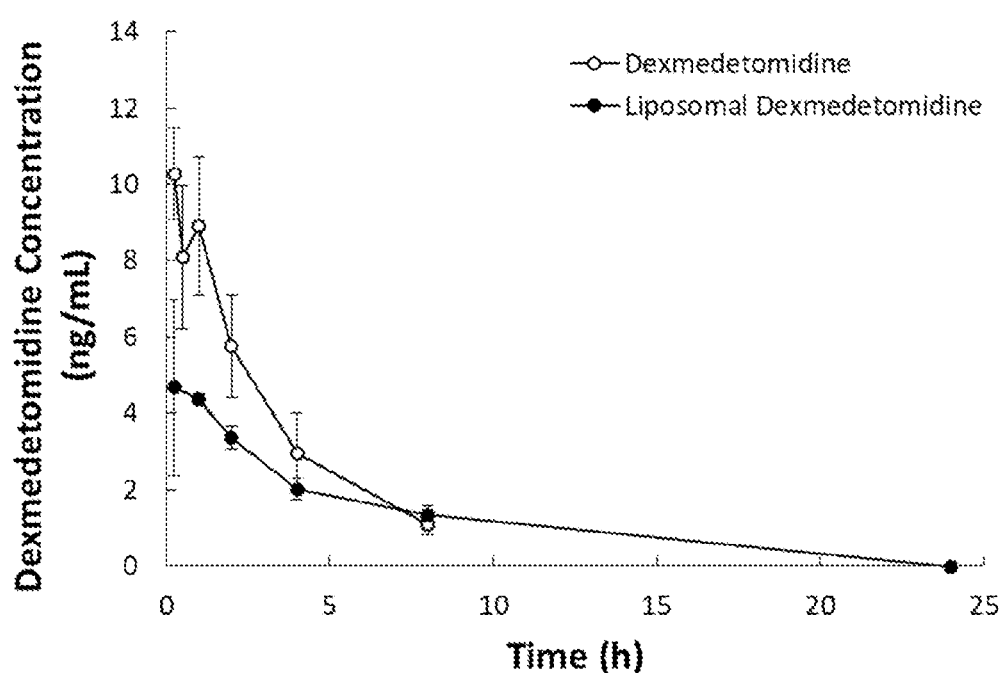
FIG. 2 is a line graph showing the plasma dexmedetomidine concentration in rats after intramuscular injection of liposomal dexmedetomidine and free dexmedetomidine.

In addition, FIG. 2 shows dexmedetomidine was undetectable in the plasma of rats 8-hour post IM injection of free dexmedetomidine whereas dexmedetomidine was detected in the plasma of rats 24-hour post IM injection of liposomal dexmedetomidine formulation. The results support a conclusion that the claimed pharmaceutical composition sustained the release of dexmedetomidine.

Example 5. Pharmacodynamic (PD) Study of Liposomal Dexmedetomidine Formulation An in vivo PD evaluation of the liposomal dexmedetomidine formulation was performed using male guinea pigs (600±100 g). The guinea pigs were housed in a holding room which operated on a 12-hr light/12-hr dark circadian cycle with free access to water and food.

Figure 3A:
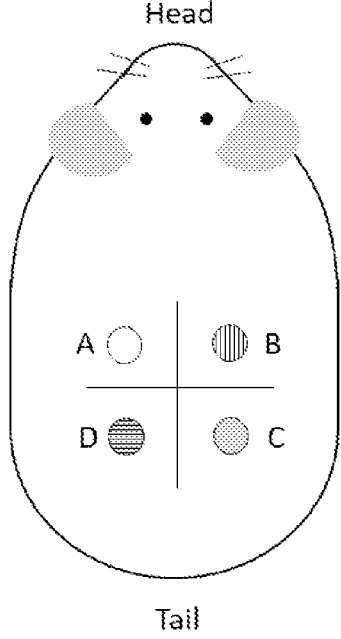
FIG. 3A illustrates schematically the four injections administered to the back of the guinea pig.

Four guinea pigs were used in this study and each guinea pig received 4 intracutaneous injections of 4 different formulations on its back to create 4 individual wheals respectively (i.e., 4 wheals per formulation), as illustrated in FIG. 3A. The 4 formulations are: (A) 1.5 mg of free ropivacaine, prepared by dissolving ropivacaine hydrochloride monohydrate (Focus Synthesis) in 9.4% sucrose solution at 18.0 mg/mL, (B) 1.5 mg of free ropivacaine and 0.2 μg of liposomal dexmedetomidine formulation prepared according to Example 1, (C) 1.5 mg of liposomal ropivacaine composition and (D) 1.5 mg of liposomal ropivacaine composition and 0.2 μg of liposomal dexmedetomidine formulation prepared according to Example 1. The liposomal ropivacaine composition was disclosed in PCT/US18/48329. Briefly, 339.0 mg of DMPC, 96.7 mg of cholesterol and 200.0 mg of ropivacaine were dissolved in 10 mL of tert-butanol and lyophilized. The lyophilized cake was hydrated with a 50 mM histidine solution, pH 6, to form multilamellar vesicles (MLVs) with entrapped ropivacaine (liposomal ropivacaine composition), and the concentration of ropivacaine was diluted to 15.0 mg/mL with 9.4% sucrose solution. The anesthesia effect of ropivacaine was assessed at 30 minutes (0.5 hour), 1.0, 1.5, 2.0, 2.5, 3.0, 3.5, 4.0, 5.0, 6.0, 7.0, 8.0, 10 and 24 hours post-injection. The anesthetic effect was determined by observing the guinea pig's response to stimuli around individual wheals (pin prick test). PD data obtained from the pin prick tests were analyzed using an inhibitory effect sigmoid Emax model in PKSolver (Comput Methods Programs Biomed. 2010; 99(3):306-314). The PD parameters of the ropivacaine with and without the L-DEX are summarized in Table 3Table 3.

The results in Table 3 show the addition of the liposomal dexmedetomidine formulation increase the $TE_{50}$ (time to half maximal effect, the time to achieve a response halfway between the baseline and maximum after the administration of a single, specified dose) of free ropivacaine and liposomal ropivacaine composition and extended the duration of anesthesia induced by free ropivacaine and liposomal ropivacaine composition by about 1.4-fold.

TABLE 3

PD parameters derived from the guinea pigs receiving
intracutaneous injection of 4 formulations.

| Parameters | Unit | Free Ropivacaine (A) | Free Ropivacaine + L-DEX (B) | Liposomal Ropivacaine Composition (C) | Liposomal Ropivacaine Composition + L-DEX (D) |
|---|---|---|---|---|---|
| $TE_{50}$ | h | 4.5 | 6.4 | 6.0 | 8.3 |

Figure 3B:
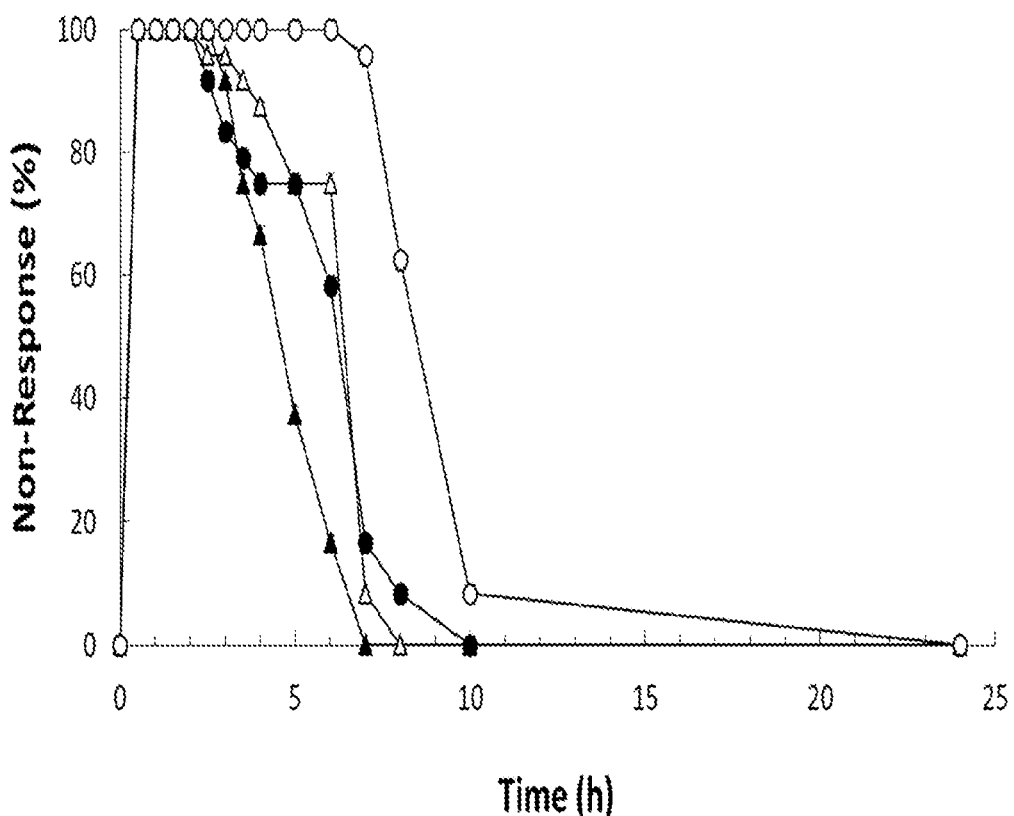
FIG. 3B is a line graph showing the non-response rate of guinea pigs to pain stimulus after intracutaneous injection of (a) free ropivacaine, (b) free ropivacaine plus liposomal dexmedetomidine (L-DEX), (c) liposomal ropivacaine composition or (d) liposomal ropivacaine composition plus L-DEX.

In addition, FIG. 3B shows the duration of anesthesia induced by free ropivacaine or liposomal ropivacaine composition was extended with the co-administration of L-DEX.

The results support a conclusion that the claimed pharmaceutical composition is an effective adjuvant of an anesthetic.

Example 6. Pharmacodynamic (PD) Study of Liposomal Dexmedetomidine Formulation Another in vivo PD study to evaluate the feasibility of the liposomal dexmedetomidine formulation as an adjuvant medicament injected at a distant site for pain management was performed according to the method of Example 5.

Figure 4A:
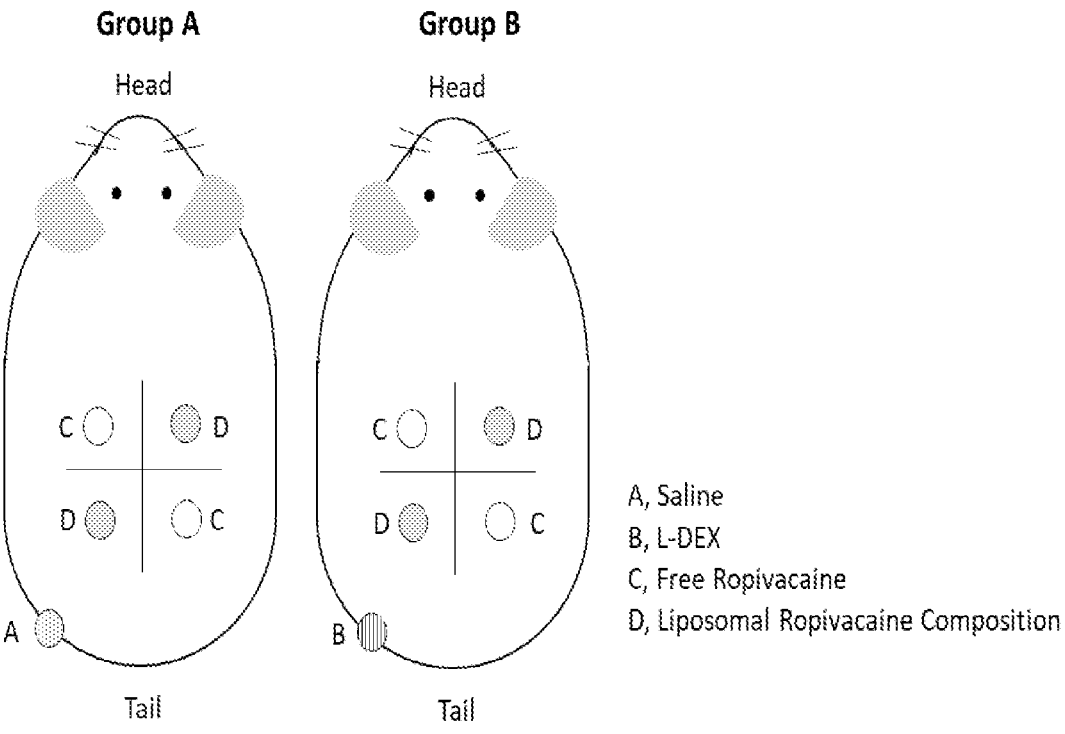
FIG. 4A illustrates schematically the intramuscular injection sites (A and B) and the intracutaneous injection sites (C and D) of Group A and Group B guinea pigs.

Four guinea pigs were used in this study and was divided into two groups (Groups A and B). As illustrated in FIG. 4A, the guinea pigs in Group B (n=2) received an intramuscular injection of 2.0 μg/kg of L-DEX prepared according to Example 1 in its left dorsal flank (site B of FIG. 4A, outside the pin prick testing area) and the guinea pigs in Group A (n=2) received a intramuscular saline injection in its left dorsal flank (site A of FIG. 4A, outside the pin prick testing area). Each guinea pig in Group A and Group B received 4 intracutaneous injections on its back. Of the 4 intracutaneous injections, 2 injections delivered 1.5 mg of free ropivacaine each and the other two injections delivered 1.5 mg of liposomal ropivacaine composition each. The anesthetic effect of ropivacaine was assessed at 30 minutes (0.5 hour), 1.0, 1.5, 2.0, 2.5, 3.0, 3.5, 4.0, 5.0, 6.0, 7.0, 8.0 and 10 hours post-injection. The anesthetic effect was determined by observing the guinea pig's response to stimuli around individual wheals (i.e., pin prick test). PD data obtained from the pin prick tests was analyzed using an inhibitory effect sigmoid Emax model in PKSolver (Comput Methods Programs Biomed. 2010; 99(3):306-314). The PD parameters of the free ropivacaine and liposomal ropivacaine composition with or without the liposomal dexmedetomidine formulation are summarized in Table 4.

The results in Table 4 show the administration of L-DEX increased $TE_{50}$ of free ropivacaine and liposomal ropivacaine composition and extended the duration of anesthetic effect of free ropivacaine and liposomal ropivacaine composition by about 1.1- to 1.6-times.

TABLE 4

PD parameters derived from guinea pigs receiving intracutaneous
injections of free ropivacaine and liposomal ropivacaine
composition with or without L-DEX.

| Parameters | Unit | Free Ropivacaine + Saline | Free Ropivacaine + L-DEX | Liposomal Ropivacaine Composition + Saline | Liposomal Ropivacaine Composition + L-DEX |
|---|---|---|---|---|---|
| Non-response time | h | 0.5 | 1.5 | 1.0 | 3.0 |
| $TE_{50}$ | h | 1.6 | 2.5 | 5.1 | 5.5 |

Figure 4B:
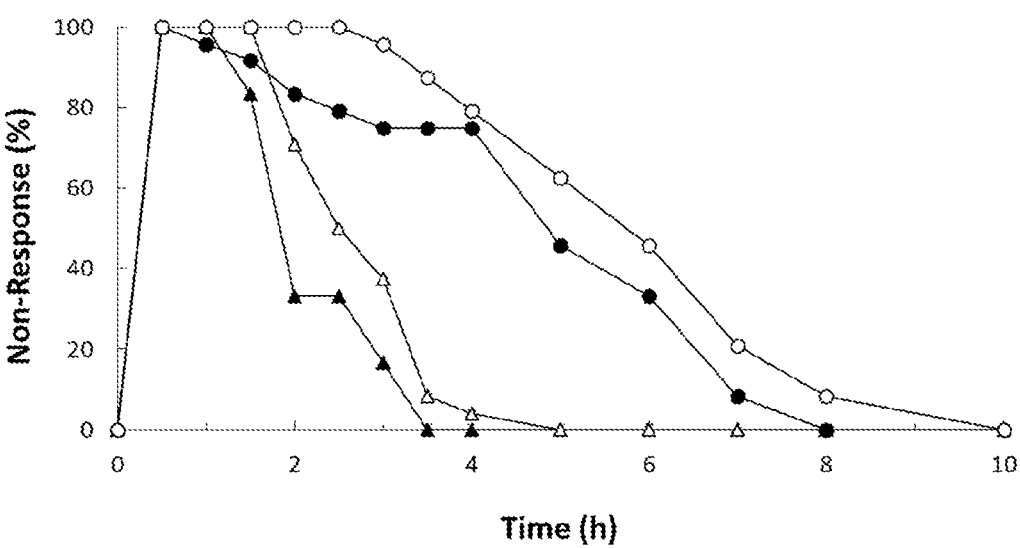
FIG. 4B is a line graph showing the effect of saline or liposomal dexmedetomidine administered outside the pin prick area of guinea pigs with the free ropivacaine or liposomal ropivacaine composition administered inside the pin prick area of the guinea pigs.

In addition, FIG. 4B shows the duration of the anesthetic effect of ropivacaine was extended even with the distant delivery (i.e., delivery outside the pin prick testing area) of liposomal dexmedetomidine formulation. The results support a conclusion that the claimed pharmaceutical composition is an effective adjuvant of an anesthetic.

The invention claimed is:
1. A pharmaceutical composition, comprising
(a) a first liposome comprising a bilayer membrane, said bilayer membrane comprises a mixture of a first lipid that is hydrogenated soy phosphatidylcholine (HSPC), 1,2-distearoyl-sn-glycero-3-phosphocholine (DSPC) or any combination thereof, cholesterol, and optionally a second lipid that is a phosphatidylethanolamine (PE), a phosphatidylglycerol (PG) or any combination thereof, wherein the mole percent of the first lipid is between 45-80%, the mole percent of cholesterol is 20-55% and the mole percent of the second lipid is 0.1-25%;

(b) a trapping agent selected from the group consisting of triethylammonium sucrose octasulfate, ammonium sulfate, ammonium phosphate, dextran sulfate and any combination thereof; and (c) a sedative drug that is dexmedetomidine, wherein the molar ratio of the sedative drug to the first lipid and the second lipid is equal to or higher than about 0.19 and wherein the sedative drug is encapsulated in the first liposome.

2. The pharmaceutical composition of claim 1, wherein the mean particle size of the first liposome is from about 50 nm to about 20 μm.

3. The pharmaceutical composition of claim 1, wherein the concentration of triethylammonium sucrose octasulfate is about 10 to about 200 mM.

4. The pharmaceutical composition of claim 1, wherein the concentration of ammonium sulfate is about 100 to about 600 mM.

5. The pharmaceutical composition of claim 1, wherein the concentration of ammonium phosphate is about 100 to about 600 mM.

6. The pharmaceutical composition of claim 1, wherein the concentration of dextran sulfate is about 0.1 to about 20 mM.

7. The pharmaceutical composition of claim 1, wherein the encapsulation efficiency of the sedative drug in the first liposome is equal to or higher than about 40%.

8. The pharmaceutical composition of claim 1, further comprising an anesthetic, an analgesic or a combination thereof.

9. The pharmaceutical composition of claim 8, wherein the anesthetic, the analgesic or the combination thereof is encapsulated in a second liposome.

10. The pharmaceutical composition of claim 9, wherein the second liposome is a multilamellar vesicle.

11. A method for sedating a subject, comprising:
administering the pharmaceutical composition of claim 1 to the subject in need of sedation.

12. A method for treating pain in a subject, comprising the step of administering:
(a) the pharmaceutical composition of claim 1, and
(b) an anesthetic, an analgesic or a combination thereof.

13. The pharmaceutical composition of claim 1, wherein the PE is N-(carbonyl-methoxypolyethyleneglycol)-1,2-distearoyl-sn-glycero-3-phosphoethanolamine (PEG-DSPE) and the PG is 1,2-dipalmitoyl-sn-glycero-3-phospho-(1'-rac-glycerol) (DPPG).

14. The pharmaceutical composition of claim 1, wherein the first lipid is HSPC, the phosphatidylethanolamine (PE) is PEG-DSPE, the phosphatidylglycerol (PG) is DPPG and the trapping agent is ammonium sulfate.

15. The pharmaceutical composition of claim 1, wherein the first lipid is HSPC, the phosphatidylethanolamine (PE) is PEG-DSPE, and the trapping agent is triethylammonium sucrose octasulfate.

16. The pharmaceutical composition of claim 1, wherein the first lipid is DSPC, the phosphatidylethanolamine (PE) is PEG-DSPE, and the trapping agent is dextran sulfate.

17. The method of claim 12, wherein the anesthetic, the analgesic or the combination thereof is encapsulated in a second liposome.

18. The method of claim 17, wherein the second liposome is a multilamellar vesicle.

19. The pharmaceutical composition of claim 1, wherein the molar ratio of the sedative drug to the first lipid and the second lipid is about 0.19 to about 0.37.

* * * * *